(12) United States Patent
Dixon et al.

(10) Patent No.: US 11,253,452 B2
(45) Date of Patent: Feb. 22, 2022

(54) METHODS AND COMPOSITIONS FOR COMBATTING COLOR LOSS

(71) Applicant: INNOSPEC LIMITED, Ellesmere Port (GB)

(72) Inventors: Nicholas John Dixon, Chester (GB); Matthew Robert Giles, Hoole (GB); Kimberley Elizabeth Griffiths, Rhyl (GB); Tony Gough, Mickle Trafford (GB); Ian Malcolm McRobbie, Mickle Trafford (GB)

(73) Assignee: Innospec Limited, Cheshire (GB)

( * ) Notice: Subject to any disclaimer, the term of this patent is extended or adjusted under 35 U.S.C. 154(b) by 17 days.

(21) Appl. No.: 16/095,544

(22) PCT Filed: Apr. 21, 2017

(86) PCT No.: PCT/GB2017/051111
§ 371 (c)(1),
(2) Date: Oct. 22, 2018

(87) PCT Pub. No.: WO2017/182819
PCT Pub. Date: Oct. 26, 2017

(65) Prior Publication Data
US 2019/0091119 A1 Mar. 28, 2019

(30) Foreign Application Priority Data

Apr. 22, 2016 (GB) ........................... 1607042
Sep. 30, 2016 (GB) ........................... 1616645

(51) Int. Cl.
*A61K 8/34* (2006.01)
*A61Q 5/00* (2006.01)
(Continued)

(52) U.S. Cl.
CPC .............. *A61K 8/34* (2013.01); *A61K 8/33* (2013.01); *A61Q 5/004* (2013.01); *C07C 47/19* (2013.01);
(Continued)

(58) Field of Classification Search
CPC ........ A61K 8/34; A61K 8/33; A61K 2800/87; A61K 2800/884; A61K 8/342;
(Continued)

(56) References Cited

U.S. PATENT DOCUMENTS 4,932,977 A  6/1990 Schultz
5,573,553 A * 11/1996 McBride .............. D06M 15/59
                                                427/372.2
(Continued)

FOREIGN PATENT DOCUMENTS

GB   2075560 A    11/1981
JP   11199448 A1   7/1999
(Continued)

OTHER PUBLICATIONS

English translation of WO0230373A2 (Year: 2002).*
(Continued)

*Primary Examiner* — Quanglong N Truong
(74) *Attorney, Agent, or Firm* — Carlos A. Fisher; Stout, Uxa & Buyan, LLP

(57) ABSTRACT

A method of combating colour loss from a dyed material, the method comprising contacting the material with a composition comprising a hydroxy-substituted aldehyde.

19 Claims, 1 Drawing Sheet

(51) Int. Cl.
*D06P 5/04* (2006.01)
*A61K 8/33* (2006.01)
*C07C 47/19* (2006.01)
*D06P 3/14* (2006.01)

(52) U.S. Cl.
CPC ............ *D06P 5/04* (2013.01); *A61K 2800/87* (2013.01); *A61K 2800/884* (2013.01); *D06P 3/14* (2013.01)

(58) Field of Classification Search
CPC .... A61K 8/345; A61K 2800/51; C07C 47/19; A61Q 5/004; A61Q 5/00; A61Q 5/065; A61Q 5/12; D06P 5/04; D06P 3/14; D06P 3/148
See application file for complete search history.

(56) References Cited

U.S. PATENT DOCUMENTS

| | | | |
|---|---|---|---|
| 7,766,976 | B2 | 8/2010 | Bureiko |
| 8,551,188 | B2 | 10/2013 | Lalleman |
| 10,799,440 | B2 | 9/2020 | Gough |
| 2005/0138739 | A1 | 6/2005 | Henning et al. |
| 2008/0104772 | A1 | 5/2008 | Gross et al. |
| 2008/0313821 | A1 | 12/2008 | Lalleman et al. |
| 2011/0117147 | A1* | 5/2011 | Ishida ............... C07C 69/24 424/401 |
| 2015/0034117 | A1 | 2/2015 | Pressly et al. |
| 2015/0034119 | A1 | 2/2015 | Pressly et al. |
| 2019/0091120 | A1 | 3/2019 | Gough |
| 2019/0091121 | A1 | 3/2019 | Dixon |

FOREIGN PATENT DOCUMENTS

| | | |
|---|---|---|
| JP | 2001055672 A | 2/2001 |
| JP | 2007191475 A | 8/2007 |
| WO | 2002003937 A2 | 1/2002 |
| WO | 2002030373 A2 | 4/2002 |
| WO | 2003090700 A1 | 11/2003 |
| WO | 2015074971 A1 | 5/2015 |
| WO | 2016078970 A1 | 5/2016 |
| WO | 2018060719 A1 | 5/2018 |
| WO | 2018060720 A1 | 5/2018 |

OTHER PUBLICATIONS

Lalleman et al. (FR 2937543 A1 Abstract English machine translation) hereinafter Lalleman (Year: 2010).*
International Search Report and Written Opinion dated Jul. 3, 2017, for international application No. PCT/GB2017/051111 international filing date Apr. 21, 2017.
United Kingdom Combined Search and Examination Report dated Jan. 22, 2018, for Application No. GB 1706349.6.
United Kingdom Combined Search and Examination Report dated Feb. 8, 2017 for Application No. GB 1607042.7.
Donald Craig, et al., Additive Pummerer reactions of vinylic sulphoxides. Synthesis of γ-hydroxy-α,β unsaturated esters and α-hydroxyketones, Tetrahedron Letters, vol. 31, No. 44, 1990, pp. 6441-6444.
Anita Mlakar, et al., Reinvestigation of lipid peroxidation of linolenic acid, Biochimica et Biophysica Acta, vol. 1214, 1994, pp. 209-220.
International Preliminary Report on Patentability dated Oct. 23, 2018, for international PCT/GB2017/051111.

* cited by examiner

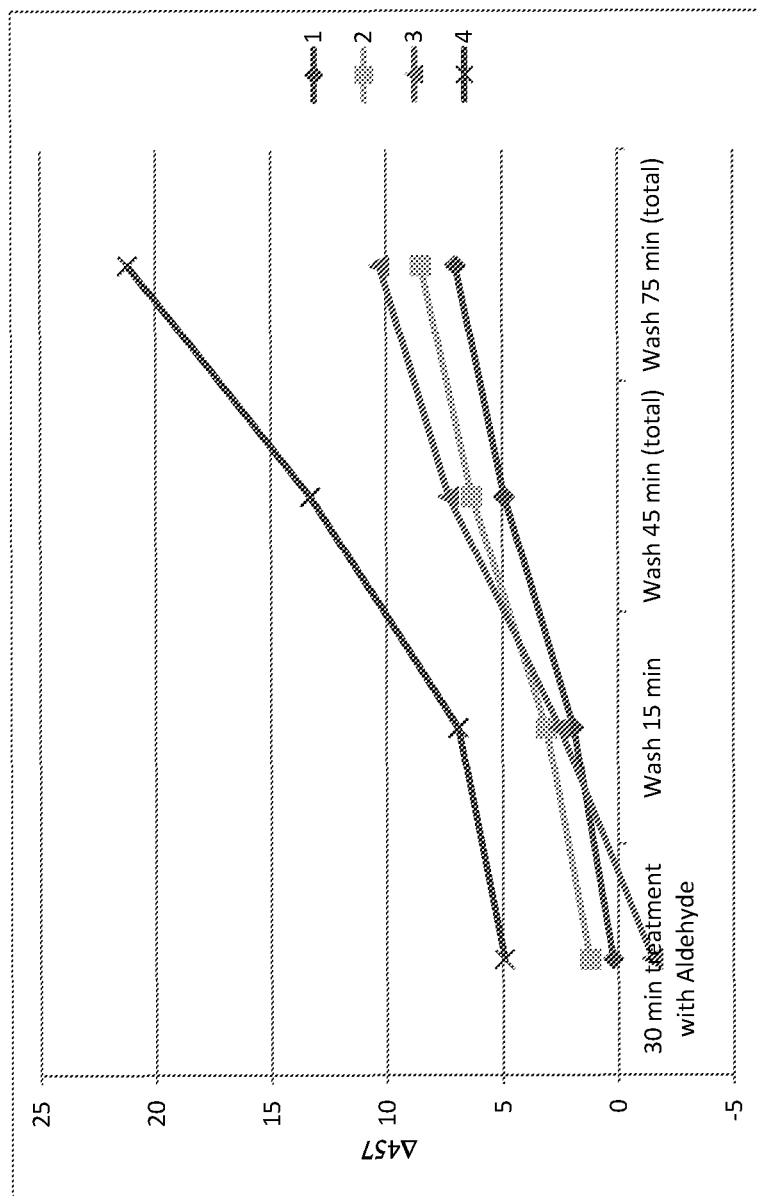

METHODS AND COMPOSITIONS FOR COMBATTING COLOR LOSS

CROSS-REFERENCE TO RELATED APPLICATIONS

This application is a U.S. national stage application under 35 U.S.C. 371 of co-pending International Application No. PCT/GB2017/051111 filed on Apr. 21, 2017, which in turn claims priority to GB Application No. 1607042.7 filed on Apr. 22, 2016, which in turn claims priority to GB Application No. 1616645.6 filed on Sep. 30, 2016, the contents of which are incorporated by reference herein in their entireties for all purposes.

The present invention relates to a method of treating a dyed material, to compositions for use in such methods and to uses relating thereto. In particular the present invention relates to a method of treating a dyed keratinous material, especially hair. The method is especially useful for reducing, inhibiting or preventing the loss of colour from dyed materials, especially dyed hair.

Procedures for dyeing materials, especially hair and other keratinous materials, have been in existence for many years. However the dyed materials lose colour intensity and vibrancy after dyeing. One cause of this loss of colour is believed to be leaching of dye molecules from the materials when in contact with water or other solvents which can dissolve/solubilise the dyes and cause them to diffuse out of the material. This colour loss can thus occur during processes such as washing of the material (or shampooing in the case of hair) or during other processes where the material comes into contact with water or other solvents that can leach dyes from the material. The problem is greater in the case of small dye molecules as these are more mobile and can thus be leached from the material at a faster rate than larger dye molecules. As a result, repeated washing of materials can lead to colour loss over time. This can also cause a colour shift, for example whereby one or more dye compounds present in a mixture used to colour a material are leached from the material to a greater extent than the others during washing.

For textile materials and fabrics colour loss can occur during washing of the material, either in a hand washing process or in an automatic washing machine.

One effective means by which colour loss can be prevented or inhibited is by treatment with formaldehyde. However formaldehyde is a suspected carcinogen and thus its use in cosmetic compositions is strictly regulated and highly undesirable. There have been several attempts to provide alternative means for combatting colour loss from hair. However to date none of these have been completely satisfactory and there therefore exists a need to develop further alternative strategies.

It is an aim of the present invention to provide means for reducing, inhibiting or preventing colour loss from dyed materials.

According to a first aspect of the present invention there is provided a method of combating colour loss from a dyed material, the method comprising contacting the material with a composition comprising a hydroxy-substituted aldehyde.

The present invention relates to a method of combating colour loss from a dyed material. The method may involve treating a material which has been dyed and/or it may involve treating a material which is going to be dyed and/or it may involve treating a material as part of the dyeing process. The method may be used to treat any material which has been dyed/is being dyed by any means.

In some embodiments the method of the present invention may be used to combat colour loss from a dyed textile material. In such embodiments the dyed textile material suitably comprises wool and preferably comprises wool as a major proportion thereof.

In preferred embodiments the material is a keratinous material. More preferably the material comprises keratinous fibres. Preferably the material is hair. The hair may be human or animal hair. In especially preferred embodiments the method of the present invention is a method treating human hair. Most preferably it is a method of treating human hair growing on the head.

However it will be appreciated that the method of the present invention can also be used to combat colour loss from hair that is not still growing (i.e. has been removed), such as a wig or animal hair, for example wool.

In especially preferred embodiments the present invention relates to a method of treating dyed hair to combat colour loss. The method may be used to combat colour loss, from hair that has been dyed by any means. For example the invention may be used to combat colour loss from hair that has been dyed using direct dyes. The types of compounds that are classified as direct dyes for hair will be known to the person skilled in the art and include nitrophenylenediamine compounds (eg, 2-nitro-o-phenylenediamine, HC Yellow 10, HC Red 14, N,N-bis-(2-hydroxyethyl)-2-nitro-p-phenylenediamine, HC Violet 2 and HC Blue 2); nitroaminophenol compounds (eg, HC Yellow 4, 2-amino-3-nitrophenol, HC Orange 3, 4-hydroxypropylamino-3-nitrophenol and 3-nitro-p-hydroxyethylaminophenol); and anthraquinone compounds (eg, Disperse Red 11, Disperse Violet 4, Disperse Blue 3 and HC Blue 14). However the method of the present invention is particularly effective at preventing colour loss from hair that has been dyed using oxidative dyes.

Oxidative dyeing of hair is commonly used for permanent, semi-permanent or demi-permanent colouration of the hair. It involves treatment of the hair with small substituted aromatic compounds (for example phenols, naphthols, phenylene diamines and amino phenols (known as intermediates)) which are oxidised to produce the active dye molecules in situ. Hair colouring methods of this type will be very well known to persons skilled in the art.

The method of the present invention involves contacting the material, preferably hair, with a composition comprising a hydroxy-substituted aldehyde.

In some embodiments the method of the first aspect of the present invention is not a method of dyeing a material, such as hair but rather it is a method of treating a dyed material.

The present invention thus suitably provides a method of treating hair that has already been dyed. In such embodiments the composition used in the method suitably does not contain any compounds that dye the hair. Preferably the method is carried out at least 12 hours, preferably at least 24 hours after the hair has been dyed.

In some embodiments the method may be carried out any time prior to, during or shortly after dyeing the material, as part of the dyeing process.

In embodiments in which the method of the first aspect is carried out shortly before, during or shortly after dyeing the hair, the present invention may further provide an improved hair colouring method. By shortly before or after dyeing we mean preferably within 2 hours, more preferably within 1 hour, suitably within 30 minutes.

According to a second aspect of the present invention there is provided a method of colouring hair, the method comprising:
(a) contacting the hair with a colouring composition; and
(b) contacting the hair with a composition comprising a hydroxy-substituted aldehyde.

The present invention relates to a method of colouring hair using a colouring composition. This may also be referred to herein as a method of dyeing hair using a dyeing composition.

The method of the second aspect is a method of colouring hair. By this we mean to include colouring human hair or colouring animal hair, including wool. Preferably the method of the second aspect is a method of colouring human hair. More preferably it is a method of colouring human hair growing on the head.

Steps (a) and (b) may be carried out separately in any order or they may be carried out simultaneously.

In some embodiments step (b) is carried out before step (a) and thus the method involves a step of pre-treating hair with a composition comprising a hydroxyaldehyde prior to dyeing.

In some embodiments steps (a) and (b) may be carried out simultaneously and the method involves contacting the hair with a colouring composition comprising a hydroxy aldehyde.

In some preferred embodiments step (b) is carried out after step (a). Suitably the hair is rinsed and optionally dried between step (a) and step (b).

Step (a) may involve contacting the hair with any suitable colouring composition. Such compositions will be known to the person skilled in the art.

In some preferred embodiments step (a) may involve forming the colouring composition in the hair in situ by applying dye precursor compounds and an oxidising composition (a developer) in an oxidative dyeing method.

In some embodiments step (a) may involve contacting the hair with a colouring composition comprising one or more direct dyes.

In some embodiments the method of the first aspect of the present invention is not carried out as part of the dyeing process and the composition contacted with the hair may be in the form of a shampoo composition, a conditioning composition, a hair styling composition, a hair permanent waving composition, a hair permanent straightening composition, a hair relaxing composition or a subsequent hair colouring/hair dyeing composition.

Compositions which perform multiple functions, for example combined shampoo and conditioning compositions are also within the scope of the invention.

According to a third aspect of the present invention there is provided a composition comprising a hydroxy-substituted aldehyde.

Preferred features of the first, second and third aspects of the invention will now be described. Any feature may apply to any other aspect as appropriate. Thus the method of the first aspect and the method of the second aspect may suitably involve contacting the hair with a composition comprising a hydroxy-substituted aldehyde as defined in relation to the third aspect.

The composition of the third aspect of the present invention comprises a hydroxy-substituted aldehyde.

Any suitable hydroxy-substituted aldehyde may be included.

Suitable aldehydes for use herein have at least 2 carbon atoms. Preferably they have at least 3 carbon atoms.

Suitable aldehydes for use herein may have up to 36 carbon atoms, preferably up to 30 carbon atoms, more preferably up to 24 carbon atoms, preferably up to 20 carbon atom, for example up to 18 carbon atoms or up to 16 carbon atoms.

Some preferred aldehydes for use herein have from 3 to 20 carbon atoms, for example 3 to 16 carbon atoms.

Some preferred aldehydes for use herein have from 3 to 12 carbon atoms, for example 3 to 11 carbon atoms.

Some especially preferred aldehydes for use herein have from 3 to 9 carbon atoms, more preferably from 3 to 8 carbon atoms.

Some other preferred aldehydes for use herein have from 8 to 16 carbon atoms, for example 10 to 14 carbon atoms.

In some preferred embodiments the hydroxy-substituted aldehyde contains only one aldehyde functional group.

The aldehyde may comprise one or more hydroxy substituents.

Suitably the aldehyde comprises one, two or three hydroxy substituents, preferably one or two substituents.

In some preferred embodiments the aldehyde is not a saccharide.

Preferably the aldehyde comprises one hydroxy substituent.

Suitably the aldehyde has a hydroxy substituent at the 2, 3 or 4 position.

In some embodiments the aldehyde may have a hydroxy substituent at the 2 and 3 or the 2 and 4 positions.

Suitably the aldehyde may have a hydroxy substituent at the 2 position and/or the 3 position.

Suitably the aldehyde may have a hydroxy substituent at the 2 position or the 3 position.

In especially preferred embodiments the aldehyde has a hydroxy substituent at the 2 position. Thus the aldehyde is suitably an α-hydroxy aldehyde/a 2-hydroxy aldehyde.

The aldehyde has a hydroxy substituent. It may have one or more further substituents.

Suitable further substituents may be selected from a further hydroxy substituent, a further aldehyde group, a keto group, a carboxy group, an acyl group, a halo group, an alkoxy group, an alkyl group, a nitro group, an amino group, a sulfoxy group, a mercapto group, an amide, an ester, a nitrile group or an isonitrile group.

Preferred halo substituents are chloro, fluoro, and bromo.

Preferred alkoxy substituents are methoxy, ethoxy, propoxy and butoxy, including isomers thereof.

Preferred alkyl substituents are $C_1$ to $C_8$ alkyl, preferably $C_1$ to $C_6$ alkyl, including isomers thereof.

In some embodiments the hydroxyaldehyde may include a further aldehyde functional group. Suitably such further aldehyde groups may be α-substituted.

In preferred embodiments the aldehyde includes a hydrocarbon chain. This is suitably a chain with a carbon backbone. However compounds in which the carbon backbone is interrupted by one or more heteroatoms are also within the scope of the invention. For example the carbon backbone may be interrupted by one or more oxygen, sulfur or nitrogen molecules and thus the aldehyde may include an ether, a thioether, an amine or a disulfide moiety.

The aldehyde may be predominantly aliphatic or predominantly aromatic in nature. Preferably the aldehyde is aliphatic. However it may include one or more double bonds and/or one or more cyclic groups. It may be straight-chain or branched.

In some especially preferred embodiments the aldehyde has the formula (I):

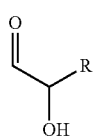

(I)

wherein R is hydrogen or an optionally substituted hydrocarbyl group having 1 to 30 carbon atoms.

R may be hydrogen or an optionally substituted alkyl, alkenyl or aryl group having 1 to 30 carbon atoms, preferably 1 to 20 carbon atoms, more preferably 1 to 10 carbon atoms.

Preferably R is hydrogen or an optionally substituted alkyl or alkenyl group having 1 to 30, preferably 1 to 20, suitably 1 to 10 carbon atoms.

In some embodiments R is an optionally substituted alkyl or alkenyl group having 1 to 7, preferably 1 to 6 carbon atoms.

In some embodiments R is an optionally substituted alkyl or alkenyl group having 8 to 14, preferably 8 to 12 carbon atoms.

R may be substituted with one or more substituents selected from keto, hydroxy, halo, carboxy, acyl, nitro, amino, mercapto, alkoxy, sulfoxy, ester, nitrile, isonitrile or amide. The carbon backbone may be interrupted by one or more heteroatoms, for example one or more oxygen, nitrogen or sulfur atoms.

In some preferred embodiments R is an unsubstituted alkyl group having 1 to 8, preferably 1 to 6 carbon atoms.

In preferred embodiments R is an unsubstituted alkyl group having 4 to 16, preferably 8 to 12 carbon atoms.

R may be selected from hydroxy methylene, methyl, butyl, hexyl, octyl, decyl and dodecyl. These groups may be straight-chained or branched. Preferably they are straight-chained.

Suitably R is selected from hydroxy methylene, methyl, n-butyl and n-hexyl.

R may be selected from methyl, n-butyl, n-hexyl n-octyl, n-decyl and n-dodecyl.

Preferably R is selected from methyl, n-butyl and n-hexyl.

Most preferably R is selected from n-butyl and n-hexyl.

In some preferred embodiments the aldehyde is a hydroxy-substituted aliphatic aldehyde.

Suitable hydroxy-substituted aldehydes for use herein include 2-hydroxydecanal, 2-hydroxydodecanal, 2-hydroxytetradecanal, 2-hydroxyhexanal, 2-hydroxyoctanal, 2-hydroxypropanal, glyceraldehyde, 6-hydroxyhexanal, 3-hydroxypropanal, 4-hydroxy-but-2-enal, 2-hydroxybutanal, 3-hydroxybutanal and 4-hydroxybutanal.

Suitable hydroxy-substituted aldehydes for use herein include 2-hydroxydecanal, 2-hydroxydodecanal, 2-hydroxytetradecanal, 2-hydroxyhexanal, 2-hydroxyoctanal, 2-hydroxypropanal, 6-hydroxyhexanal, 3-hydroxypropanal, 4-hydroxy-but-2-enal, 2-hydroxybutanal, 3-hydroxybutanal and 4-hydroxybutanal.

Preferred hydroxy-substituted aldehydes for use herein include 2-hydroxyhexanal, 2-hydroxyoctanal, 2-hydroxypropanal, glyceraldehyde, 6-hydroxyhexanal, 3-hydroxypropanal, 4-hydroxy-but-2-enal, 2-hydroxybutanal, 3-hydroxybutanal and 4-hydroxybutanal.

Preferred hydroxy-substituted aldehydes for use herein include 2-hydroxyhexanal, 2-hydroxyoctanal, 2-hydroxypropanal, 6-hydroxyhexanal, 3-hydroxypropanal, 4-hydroxy-but-2-enal, 2-hydroxybutanal, 3-hydroxybutanal and 4-hydroxybutanal.

More preferred hydroxy-substituted aldehydes for use herein include 2-hydroxyhexanal, 2-hydroxyoctanal, 2-hydroxypropanal and glyceraldehyde.

Most preferred hydroxy-substituted aldehydes for use herein are 2-hydroxyhexanal and 2-hydroxyoctanal and 2-hydroxypropanal.

Suitably the composition comprises a hydroxy-substituted aldehyde in the amount of at least 0.1 wt %, suitably at least 0.5 wt %, preferably at least 1 wt %, for example at least 1.5 wt %.

The composition may comprise a hydroxy-substituted aldehyde in the amount of up to 50 wt %, preferably up to 30 wt %, suitably up to 20 wt %, preferably up to 10 wt %, more preferably up to 5 wt %, for example up to 4 wt %, up to 3 wt % or up to 2.75 wt %.

In some embodiments the composition comprises from 0.1 to 10 wt % of hydroxyaldehyde, preferably from 0.5 to 5 wt %, suitably from 0.5 to 3 wt %.

In some alternative embodiments the composition may comprise much greater concentrations of hydroxyaldehyde, for example from 20 to 100 wt %, preferably from 50 to 100 wt %, for example from 70 to 100 wt % or from 90 to 100 wt %.

The composition of the third aspect may comprise a mixture of two or more hydroxy-substituted aldehydes. In such embodiments the above amounts refer to the total amount of all such compounds present in the composition.

In some embodiments the composition of the third aspect comprises a mixture of two or more hydroxy-substituted aldehydes.

In some embodiments the composition of the third aspect comprises 2-hydroxyoctanal and one or more further hydroxy-substituted aldehydes.

In some embodiments the composition of the third aspect comprises glyceraldehyde and one or more further hydroxy-substituted aldehydes.

In some embodiments the composition of the third aspect comprises 2-hydroxyoctanal and glyceraldehyde. It may optionally comprise one or more further hydroxy-substituted aldehydes.

In some embodiments the composition comprises less than 0.1 wt % glyceraldehyde, suitably less than 0.01 wt %. Suitably the composition does not comprise glyceraldehyde.

In some embodiments the composition of the third aspect comprises a first hydroxy-substituted aldehyde having less than 10 carbon atoms and a second hydroxy-substituted aldehyde having 10 or more carbon atoms. It may optionally comprise one or more further hydroxy-substituted aldehydes. For example the composition of the third aspect may comprises a first hydroxy-substituted aldehyde having 3 to 9 carbon atoms, preferably 3 to 8 carbon atoms and a second hydroxy-substituted aldehyde having 10 to 18 carbon atoms, preferably 10 to 16 carbon atoms, more preferably 10 to 14 carbon atoms. It may optionally comprise one or more further hydroxy-substituted aldehydes.

In some embodiments the composition of the third aspect comprises one or more hydroxy-substituted aldehydes selected from 2-hydroxydecanal, 2-hydroxydodecanal and 2-hydroxytetradecanal and one or more further hydroxy-substituted aldehydes selected from 2-hydroxyhexanal, 2-hydroxyoctanal, 2-hydroxypropanal, glyceraldehyde, 6-hydroxyhexanal, 3-hydroxypropanal, 4-hydroxy-but-2-enal, 2-hydroxybutanal, 3-hydroxybutanal and 4-hydroxybutanal.

In some embodiments the composition of the third aspect comprises one or more hydroxy-substituted aldehydes selected from 2-hydroxydecanal, 2-hydroxydodecanal and 2-hydroxytetradecanal and one or more further hydroxy-substituted aldehydes selected from 2-hydroxyhexanal, 2-hydroxyoctanal, 2-hydroxypropanal, 6-hydroxyhexanal, 3-hydroxypropanal, 4-hydroxy-but-2-enal, 2-hydroxybutanal, 3-hydroxybutanal and 4-hydroxybutanal.

In some embodiments the composition of the third aspect may comprise one or more hydroxy-substituted aldehydes selected from 2-hydroxydecanal, 2-hydroxydodecanal and 2-hydroxytetradecanal and one or more further hydroxy-substituted aldehydes selected from 2-hydroxyhexanal, 2-hydroxyoctanal, 2-hydroxypropanal and glyceraldehyde.

In some embodiments the composition of the third aspect may comprise one or more hydroxy-substituted aldehydes selected from 2-hydroxydecanal, 2-hydroxydodecanal and 2-hydroxytetradecanal and one or more further hydroxy-substituted aldehydes selected from 2-hydroxyhexanal, 2-hydroxyoctanal and 2-hydroxypropanal.

The composition of the present invention may be provided in any suitable form. It may be in the form of a gel, paste, cream or wax. It may be in the form of a liquid composition. Such compositions may be in the form of a solution, dispersion or emulsion. It may be provided as a solid composition, for example as a powder or as a bar. In some embodiments a concentrate composition to be diluted prior to use may be provided. In some embodiments the composition of the third aspect may be part of precursor composition to be mixed with one or more further components prior to contact with the material.

The form and nature of the composition of the third aspect will depend on the intended use thereof.

In some embodiments the composition is a laundry detergent composition. In such embodiments the composition suitably comprises one or more further ingredients selected from builders, surfactants, chelating agents, bleaches, optical brighteners, enzymes, fragrances and other such ingredients commonly found in laundry detergent compositions. The composition may be a hand washing laundry detergent composition or an automatic laundry detergent composition.

In especially preferred embodiments the composition is a hair care composition.

Suitably the composition comprises one or more diluents or carriers. Preferred diluents and carriers are cosmetically approved compounds and suitable examples of these will be known to the person skilled in the art. Examples of suitable carriers include organic solvents (eg, hydrocarbon solvents (eg, isododecane), alcohols (eg, ethanol, propanol and butanol), propylene carbonate, benzyl alcohol, aliphatic or aromatic esters (eg, vegetable oils, isopropyl myristate, C12-15 alkyl benzoate), perfluorocarbon solvents, and silicone fluids.

In some embodiments the composition is an aqueous composition. Suitably water is the major solvent present in the composition. In some embodiments water provides for at least 50 wt % of all solvents present in the composition, preferably at least 60 wt %, more preferably at least 70 wt %, suitably at least 80 wt %, for example at least 90 wt % or at least 95 wt %. In some embodiments one or more further water miscible solvents may be present. Examples of suitable water miscible solvents include monohydric and polyhydric alcohols, for example ethanol, glycerol and isopropanol.

In some embodiments the composition of the present invention is not aqueous and the major diluent or carrier is an oleophilic material. In such embodiments the composition may comprise as a major solvent one or more higher fatty alcohols, a mineral oil and/or a vegetable oil.

In some embodiments the composition is substantially aqueous but the aldehyde is dispersed within an oleophilic phase in which it is soluble.

In some embodiments the composition may consist essentially of one or more hydroxy-substituted aldehydes and one more diluents or carriers. In preferred embodiments the composition comprises one or more further components. Suitable components are those typically used in personal care compositions and are known to the person skilled in the art.

As detailed above the compositions of the present invention may comprise different components depending on the intended use thereof. In some embodiments the composition may be used immediately after dyeing the hair. Alternatively the composition may be used one or more times as a hair treatment composition. In some embodiments it may be provided as a colour-loss prevention composition. Alternatively the composition may be in the form of shampoo, conditioner or hair styling product, for example a serum, wax, mousse, gel or spray or any other hair treatment form that could be used to provide general hair care benefits. Compositions which perform multiple functions, for example combined shampoo and conditioning compositions are also within the scope of the invention.

Suitably the composition comprises one or more additional components selected from surfactants (including anionic, amphoteric, nonionic and cationic surfactants); conditioning agents (including quaternary ammonium compounds, cationic polymers, silicones, synthetic or natural oils or resins etc), fatty alcohols, electrolytes or other rheology modifiers, opacifying/pearlising agents, scalp benefit agents, fragrances, dyes, UV filters, penetration enhancers (eg, propylene carbonate, benzyl alcohol etc), preservatives, antioxidants, emulsifiers, pH adjusting agents and buffers and styling polymers (eg, polyvinylpyrrolidone etc).

In some embodiments the composition comprises a pH adjusting agent.

Suitable pH adjusting agents for use herein may include lactic acid, sodium hydroxide, sodium phosphate and salts and buffers thereof.

The pH of the composition will depend on the intended use thereof. However in preferred embodiments the composition has a pH of between 3 and 9, preferably between 3.5 and 8, more preferably between 4 and 7, preferably between 4 and 6.

In some preferred embodiments the composition is a hair care composition. Suitable hair care compositions include shampoo compositions, conditioning compositions, hair styling compositions and hair permanent waving, relaxing or permanent straightening compositions, or hair colouring compositions.

Suitable further ingredients and amounts thereof to be used in hair care compositions will be known to the person skilled in the art. The relative ratios of the components and the formulation of such compositions would be within the competence of the skilled person.

Suitably the composition is a substantially aqueous composition, suitably comprising at least 50 wt % water, preferably at least 60 wt %, more preferably at least 70 wt %.

Suitably the composition comprises one or more surfactants. For example the composition may comprise from 0.1 to 60 wt % surfactants, preferably 1 to 30 wt %, suitably from 5 to 25 wt %.

Suitably the composition comprises one or more anionic surfactants. For example the composition may comprise from 0.1 to 60 wt % anionic surfactants, preferably 1 to 30 wt %, suitably from 5 to 25 wt %.

In some embodiments the composition may comprise a quaternary ammonium salt, suitably in an amount of from 0.1 to 20 wt %, preferably 0.1 to 10 wt %.

In some embodiments the composition further comprises a succinimidyl ester. Suitable compounds of this type are described in FR2937543.

Thus the present invention may provide a hair care composition comprising a hydroxy-substituted aldehyde and a succinimidyl ester.

In such embodiments the aldehyde is suitably present in an amount of from 0.1 to 50 wt %, preferably 0.1 to 10 wt %, more preferably 0.5 to 5 wt % and the succinimidyl ester is suitably present in an amount of from 0.1 to 50 wt %, preferably 0.1 to 10 wt %, more preferably 0.5 to 5 wt %.

Preferably the succinimidyl ester is a compound of formula (I):

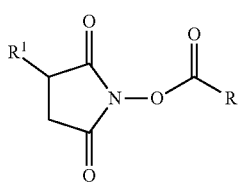

wherein R is an optionally substituted hydrocarbyl group having 5 to 36 carbon atoms; and $R^1$ is hydrogen or a solubilising group.

Preferably R is an optionally substituted alkyl, alkenyl or aryl group having 5 to 20 carbon atoms. More preferably R is selected from phenyl and $CH_3(CH_2)_n$ wherein n is 4 to 10.

Suitably $R^1$ is hydrogen or a sulfonate moiety, preferably hydrogen.

In some embodiments the composition further comprises a chelating agent. Preferred chelating agents are polycarboxylic acid-derived chelating agents.

Thus the present invention may provide a hair care composition comprising a hydroxy-substituted aldehyde and a polycarboxylic acid-derived chelating agent.

In such embodiments the aldehyde is suitably present in an amount of from 0.1 to 50 wt %, preferably 0.1 to 10 wt %, more preferably 0.5 to 5 wt % and the chelating agent is suitably present in an amount of from 0.1 to 50 wt %, preferably 0.1 to 10 wt %, more preferably 0.5 to 5 wt %.

Suitably the chelating agent is selected from glutamic acid N,N-diacetic acid (GLDA), diethylene triamine pentaacetic acid (DTPA), imido disuccinic acid (IDS), ethylene diamine tetraacetic acid (EDTA), ethylene diamine disuccinic acid (EDDS), hydroxyethyl ethylenediaminetriacetic acid (HEDTA), citric acid and mixtures thereof.

In some preferred embodiments the chelating agent is selected from DTPA, GLDA, IDS and mixtures thereof. In some especially preferred embodiments the chelating agent is selected from DTPA, GLDA and mixtures thereof.

In some embodiments the composition further comprises an amine salt of a carboxylic acid. Preferred compounds of this type are amine salts of a carboxylic acid wherein the carboxylic acid has 4 to 10 carbon atoms.

Thus the present invention may provide a hair care composition comprising a hydroxy-substituted aldehyde and an amine salt of a carboxylic acid.

In such embodiments the aldehyde is suitably present in an amount of from 0.1 to 50 wt %, preferably 0.1 to 10 wt %, more preferably 0.5 to 5 wt % and the amine salt is suitably present in an amount of from 0.1 to 50 wt %, preferably 0.1 to 10 wt %, more preferably 0.5 to 5 wt %.

Suitably the carboxylic acid has 4 to 10 carbon atoms, preferably 6 to 8 carbon atoms.

Preferably the salt is of a secondary or tertiary alkylamine and/or alkanolamine or a substituted alkylene diamine. Triethanolamine and diethanolamine are especially preferred.

Most preferably the salt is the triethanolamine or diethanolamine salt of n-hexanoic acid or n-octanoic acid.

In some embodiments the composition further comprises an amine salt of a carboxylic acid and a polycarboxylic acid derived chelating agent.

In some embodiments the composition further comprises an amine salt of a carboxylic acid, and a succinimidyl ester.

In some embodiments the composition further comprises a succinimidyl ester and a polycarboxylic acid derived chelating agent.

In some embodiments the composition further comprises an amine salt of a carboxylic acid, a succinimidyl ester and a polycarboxylic acid derived chelating agent.

In some embodiments the composition may further comprise a crosslinking agent comprising two or more reactive moieties and a linker. Compounds of this type are described for example in US2015/034117 and US2015/0034119.

In some embodiments the reactive moieties are activated carboxylic acid or sulfonic acid derivatives and the linkers are polyamino compounds which may form salts or covalent bonds with the reactive moieties.

In some embodiments the reactive moieties are maleic acid derivatives and the linker has two or more amino groups linked by alkylene or oxyalkylene chains. The crosslinking agent may be a maleimide or a maleic acid amine salt.

In some embodiments the reactive moieties are maleic acid ions and the linker comprises quaternary ammonium ions linked by alkylene or oxyalkylene chains.

Some preferred crosslinking agents have the following structures:

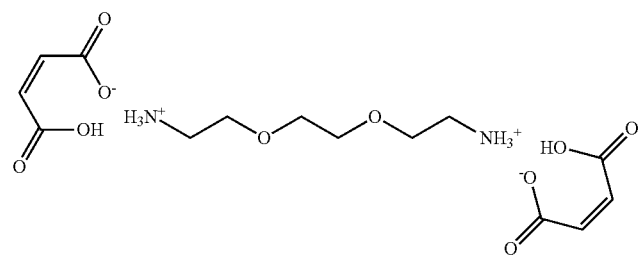

-continued

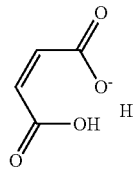 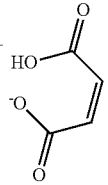

The crosslinking agent comprising two or more reactive moieties and a linker may be present in an amount of from 0.1 to 30 wt %, preferably 0.1 to 10 wt %, suitably 0.5 to 5 wt %.

In some embodiments the composition of the third aspect of the present invention is a shampoo composition.

Suitable shampoo compositions of the present invention may typically comprise 0.5 to 60 wt % of one or more anionic surfactants, preferably 1 to 50 wt %, more preferably 5 to 30 wt %, for example 8 to 20 wt % or 8 to 12 wt %; optionally from 0.1 to 30 wt % of amphoteric surfactants, preferably 1 to 15 wt %, for example 2 to 12 wt %; and optionally 0.1 to 40 wt % of non-ionic surfactants, preferably 0.5 to 30 wt %, for example 1 to 15 wt % or 2 to 12 wt %.

Shampoo compositions of the present invention may comprise one or more ingredients selected from anionic surfactants (eg, sodium laureth sulfate, sodium lauroyl methyl isethionate, sodium cocoyl methyl isethionate, sodium alpha-olefin sulfonate, sodium lauryl sulfoacetate, sodium monoalkyl phosphates, sodium dialkyl phosphates and sodium cocoyl methyl taurate, amphoteric surfactants (eg, cocamidopropyl betaine, sodium lauroamphoacetate, cocamidopropylhydroxy sultaine and disodium cocoamphodiacetate), foam boosters (eg, cocamide DEA, cocamide MEA, cocamide MIPA laureth-3), fatty alkyl alcohols (eg, cetyl alcohol, stearyl alcohol and behenyl alcohol), nonionic surfactants (eg, alkylpolyglucosides and alkyl ether ethoxylates), cationic polymers (eg, guar hydroxypropyl trimonium chloride, polyquaternium-10), silicones (eg, polydimethylsiloxanes such as dimethicone and dimethiconol), rheology modifiers (eg, carbomer, PEG-150 distearate and xanthan gum), synthetic or natural oils or resins (eg, mineral oil or vegetable oils), anti-dandruff agents (eg, piroctone olamine, zinc pyrithione and salicylic acid), styling agents (eg, polyisobutylene and polyvinyl pyrollidone/vinyl acetate copolymer), moisturising agents (eg, panthenol and glycerol), non-polymeric conditioning agents (eg, quaternary ammonium compounds such as behentrimonium chloride and stearalkonium chloride), opacifying/pearlising agents (eg, styrene/acrylates copolymer and ethylene glycol distearate), scalp benefit agents, fragrances, colouring agents, hair dyes, sunscreens, UV filters, preservatives, penetration enhancers (eg, propylene carbonate, benzyl alcohol etc) and diluents and carriers as defined herein.

Some preferred shampoo compositions of the present invention include 0.5 to 60 wt % of one or more anionic surfactants (for example, sodium laureth sulfate, sodium lauroyl methyl isethionate, sodium cocoyl isethionate, sodium alpha-olefin sulfonate, sodium lauryl sulfoacetate, sodium monoalkyl phosphates and sodium dialkyl phosphates); and 0 to 30 wt % of amphoteric surfactants (for example, cocamidopropyl betaine, sodium lauroamphoacetate and cocamidopropylhydroxy sultaine).

In some embodiments the composition of the third aspect of the present invention is a conditioning composition.

Suitable conditioning compositions of the present invention may typically comprise 0.1 to 20 wt % of one or more cationic surfactants, preferably 0.5 to 8 wt %, more preferably 1 to 4 wt %; and 0.1 to 20 wt % of one or more fatty alkyl alcohols, preferably 0.5 to 8 wt %, more preferably 1 to 4 wt %; and optionally 0.1 to 20 wt % of one or more non-ionic surfactants, preferably 0.5 to 8 wt %, more preferably 1 to 4 wt %; and optionally 0.1 to 20 wt % of one or more cationic polymers, preferably 0.5 to 8 wt %, more preferably 1 to 4 wt %.

Conditioning compositions of the present invention including rinse-off and leave-on conditioners (including 'hair masks') and hair shine or appearance enhancing products, anti-frizz treatment serums and other treatments, either leave-in or rinse-off, designed to be applied to the hair immediately after colouring or any time thereafter, and hair-tonics. Such compositions may comprise one or more further ingredients selected from: cationic surfactants including mono- and di-fatty alkyl tertiary amines and quaternary ammonium compounds (eg, mono- and di-fatty alkyl quaternary ammonium compounds, such as cetrimonium chloride, steartrimonium chloride and behentrimonium chloride), fatty alkyl alcohols (eg, cetyl alcohol, stearyl alcohol and behenyl alcohol), nonionic surfactants (eg, alkylpolyglucosides and alkyl ether ethoxylates, eg, ceteareth-20), cationic polymers (eg, guar hydroxypropyl trimonium chloride, polyquaternium-10), silicones (eg, polydimethylsiloxanes such as dimethicone and dimethiconol), rheology modifiers (eg, hydroxyethyl cellulose and polyquaternium-37), moisturising agents (eg, panthenol and glycerol), non-polymeric conditioning agents (eg, quaternary ammonium compounds such as behentrimonium chloride and stearalkonium chloride), scalp benefit agents, fragrances, colouring agents, hair dyes, sunscreens, UV filters preservatives, penetration enhancers (eg, propylene carbonate, benzyl alcohol etc), and diluents and carriers as defined herein.

Some preferred conditioning compositions of the present invention include 0.1 to 20 wt % of cationic surfactants (for example mono- and di-fatty alkyl quaternary ammonium compounds, mono- and di-fatty alkyl tertiary amines), 0.1% to 20 wt % of fatty alkyl alcohols; and 0.1% to 20 wt % of non-ionic surfactants (for example ceteareth-20).

In some embodiments the composition of the third aspect of the invention is a hair styling composition.

Suitable hair styling compositions of the present invention may typically comprise from 0.1 to 40 wt % of one or more hair styling polymers, preferably from 0.1 to 30 wt %, more preferably from 0.5 to 10 wt %.

Hair styling compositions of the present invention (including gels, mousses with and without propellant, hair sprays with and without propellant, hair pomades, hair waxes, hair creams, hair brilliantines and compositions designed to be used in conjunction with heated styling appliances such as blow dryers, curling tongs, straightening irons, hot air hoods (as used for example in hair salons)) may comprise one or more further ingredients selected from: hair styling polymers (eg, polyvinylpyrrolidone, polyvinylpyrrolidone/vinyl acetate copolymers, octylacrylamide/acrylates/butylaminoethyl methacrylate copolymer, methyl vinyl ether/maleic anhydride copolymers and polyethylene waxes), rheology modifiers (eg, carbomers, acrylates copolymers, hydroxyethylcellulose, xanthan gum and polyquaternium-37), aminomethyl propanol, fatty alkyl alcohols (eg, cetyl alcohol, stearyl alcohol and behenyl alcohol), ethanol, propyl alcohol, isopropyl alcohol, petrolatum, mineral oil, ozokerite, beeswax, carnauba wax, silicones (eg, polydimethylsiloxanes such as dimethicone and dimethiconol), polyethylene glycols, anionic surfactants (eg, sodium laureth sulfate and sodium lauroyl methyl isethionate), amphoteric surfactants (eg, cocamidopropyl betaine and disodium cocoamphodiacetate), nonionic surfactants (eg, alkylpolyglucosides and alkyl ether ethoxylates), cationic polymers (eg, guar hydroxypropyl trimonium chloride, Polyquaternium-10), silicones (eg, polydimethylsiloxanes such as dimethicone and dimethiconol), moisturising agents (eg, panthenol and glycerol), non-polymeric conditioning agents (eg, quaternary ammonium compounds such as behentrimonium chloride and stearalkonium chloride), scalp benefit agents, fragrances, colouring agents, hair dyes, sunscreens, UV filters, preservatives, penetration enhancers (eg, propylene carbonate, benzyl alcohol etc), and diluents and carriers as defined herein.

Some preferred hair styling compositions of the present invention include 0.1 to 40 wt % of one or more hair styling polymers/resins (for example polyvinylpyrrolidone, polyvinylpyrrolidone/vinyl acetate copolymers, octylacrylamide/acrylates/butylaminoethyl methacrylate copolymer, methyl vinyl ether/maleic anhydride copolymers and polyethylene waxes).

Those skilled in the art will appreciate that it is possible to confer one or more attributes of hair conditioning, shine etc, and hair styling to the hair from a single product containing the appropriate ingredients thus compositions having such combinations of hair benefit effects are also covered in the invention.

In some embodiments the composition of the third aspect is a hair permanent waving composition.

Suitable hair permanent waving compositions of the present invention may typically comprise 0.1 to 20 wt % of one or more reducing agents, preferably from 0.5 to 15 wt %, more preferably 3 to 12 wt %.

Some preferred hair permanent waving compositions of the present invention include 0.5 to 15 wt % of one or more reducing agents (for example as thioglycolic acid, ammonium thioglycolate, thiolactic acid, cysteamine, cysteine, glycerol monothioglycolate, sodium sulfite/bisulfite); alkalising agents (for example ammonia, monoethanolamine) in an amount sufficient to adjust the pH of the reducing component to between pH 8-13. Hair permanent waving compositions are typically provided in a package with a second composition comprising 0.5 to 10 wt % of one or more oxidising agents (for example hydrogen peroxide, sodium bromate, sodium percarbonate and sodium perborate) which are applied after the reducing agent composition has been applied, allowed to process and then rinsed off.

In some embodiments the composition of the third aspect of the present invention is a hair relaxing composition.

Hair relaxing compositions of the present invention may include one or more ingredients selected from sodium hydroxide, lithium hydroxide, potassium hydroxide, calcium hydroxide and guanidine carbonate. These components are suitably present in an amount of from 0.5 to 5 wt %.

Other types of permanent straightening compositions may include one or more ingredients selected from formaldehyde, glycoxylic acid, glutaraldehyde and glyoxyloyl carbocysteine. These components are suitably present in an amount of from 0.1 to 10 wt %.

The hair permanent waving, relaxing and permanent straightening compositions mentioned above may further include one or more additional ingredients selected from anionic surfactants (eg, sodium laureth sulfate and sodium lauroyl methyl isethionate), amphoteric surfactants (eg, cocamidopropyl betaine and disodium cocoamphodiacetate), quaternary ammonium compounds (eg, cetrimonium chloride, steartrimonium chloride and behentrimonium chloride), fatty alkyl alcohols (eg, cetyl alcohol, stearyl alcohol and behenyl alcohol), nonionic surfactants (eg, alkylpolyglucosides and alkyl ether ethoxylates), cationic polymers (eg, guar hydroxypropyl trimonium chloride, polyquaternium-10), silicones (eg, polydimethylsiloxanes such as dimethicone and dimethiconol), opacifying agents (eg, styrene acrylates copolymer), rheology modifiers (eg, hydroxyethyl cellulose and xanthan gum), moisturising agents (eg, panthenol and glycerol), non-polymeric conditioning agents (eg, quaternary ammonium compounds such as behentrimonium chloride and stearalkonium chloride), fragrances, sunscreens, UV filters, colouring agents and diluents and carriers as defined herein.

In some embodiments the composition of the third aspect of the present invention is a hair colouring composition.

Hair colouring compositions may include a dye compound and/or may include a dye precursor compound which forms an active dye in the hair in situ following admixture with an oxidising composition.

Oxidative hair colouring compositions of the present invention may include one or more intermediates, for example p-phenylenediamine, N,N-bis(2-hydroxyethyl)-p-phenylenediamine, p-toluenediamine, p-aminophenol phenyl methyl pyrazolone, m-phenylenediamine, resorcinol, 1-naphthol, 1-hydroxyethyl 4,5-diamino pyrazole and m-aminophenol. These intermediates can be present in any combination and ratios at a total intermediate concentration of from 0.01% to 15%, depending upon the desired shade. Such compositions typically further include one or more alkalising agents, for example ammonia, ammonium hydroxide, sodium hydroxide and monoethanolamine. Developer compositions for oxidative dyeing include an oxidising agent, for example hydrogen peroxide, sodium bromate, sodium percarbonate or sodium perborate. These are typically present in an amount of from 0.1 to 30 wt %.

Direct-dye colour compositions of the present invention may include one of more direct dyes for example from the classes of nitrophenylenediamines (eg, 4-nitro-o-phenylenediamine etc), nitroaminophenols (eg, 2-amino-4-nitrophenol etc) and am inoanthraquinones (eg, Disperse Red 11 etc). These are typically present in an amount of 0.1 wt % to 20 wt %, depending on the desired shade.

In some preferred embodiments the composition of the present invention is not a hair colouring composition. Preferably the composition comprises less than 0.1 wt %, preferably less than 0.01 wt % of dye compounds and/or dye precursor compounds. Preferably the composition does not comprise dye compounds and/or dye precursor compounds. Compounds which provide colour to the composition such as pigments and pearlescent agents may be present but suitably the composition does not include any compounds which may be used to dye hair.

In the method of the first aspect the material is contacted with a composition comprising a hydroxy-substituted aldehyde.

The material, preferably hair, may be wet or dry when contacted with the composition.

Suitably the composition is applied to the material and spread across the surface of the material. In preferred embodiments in which the material is hair the composition may be rubbed into the hair in the manner of a shampoo and/or it may be combed through the hair.

The composition of the present invention may be left on the material or it may be removed from the material. Suitably it may be rinsed using warm water.

In some embodiments the composition may be contacted with the material, spread throughout and then immediately removed.

Suitably the composition may be removed from the material by rinsing, preferably by using water.

In some embodiments the composition may be washed from the material by washing with a detergent composition.

In some embodiments the composition may be mechanically removed from the material, for example by brushing.

In some embodiments the composition may be left on the material and not removed until the material is washed during a normal cycle.

In some embodiments in which the material is hair, the composition may be applied to the hair, spread throughout and rubbed into the hair, and then rinsed with water, in the manner of a shampoo.

In some embodiments in which the material is hair, the composition may be applied to the hair, spread throughout the hair (optionally with combing), left on the hair for a short period and then rinsed from the hair with water, in the manner of a conditioner.

In some embodiments in which the material is hair, the composition may be contacted with the hair and left on the hair in the manner of a styling product. The composition may be sprayed throughout the hair, rubbed throughout the hair, combed throughout the hair or otherwise spread through the hair in a manner known to those skilled in the art.

In embodiments in which the composition is left on the hair, it suitably remains on the hair until the hair is next washed, although some of the composition may be brushed out or rubbed away during normal activity.

In the method of the present invention the composition is suitably contacted with the material, preferably hair, at ambient temperature. In some embodiments the composition may be contacted with the material at a temperature greater than the ambient temperature.

In some embodiments the composition may be contacted with the hair and the hair carrying the compositions is then heated and/or manipulated and/or dried. Thus the hair may be dried using a hairdryer or straightened after the composition is applied.

The methods of the first and second aspect of the present invention may involve heating the hair. Such a heating step may involve commonly used heating techniques such as blow drying, or using tongs, straighteners or hoods etc.

The present invention provides a method of combating colour loss from a dyed material, preferably from dyed hair. By combating colour loss we mean to include reducing the loss of colour from a dyed material and/or preventing or inhibiting the loss of colour from a dyed material, for example dyed hair.

There are a number of ways which colour loss can be measured. For example colour intensity can be measured immediately after dyeing and then after a period of time or after a number of washes. Any colour loss from a material treated according to the present invention can be compared with a control sample which is dyed and subsequently treated in an identical manner except for the use of the hydroxy-substituted aldehyde according to the invention.

Skilled experienced professionals are able to judge colour tone and intensity by sight and thus colour loss can be assessed by the naked eye. However in many cases a suitable device is used. Such devices and the operation thereof are known to the person skilled in the art and include for example chromameters or colourimeters.

A standard method of defining a colour difference is to provide a dE (or ΔE or delta E) measurement. This uses a formula to calculate colour difference based CIELAB measurements.

One suitable method of determining colour loss is to measure the reflectance of light at a particular wavelength. The difference in reflectance after time, washing or other treatment can be compared with a control. For example the reflectance of light at 457 nm could be measured (R457).

One suitable method is described in example 2.

Preferably the method of the present invention reduces colour loss by at least 10%, preferably at least 20%, more preferably at least 30%, for example at least 40%.

In some embodiments, the method of the present invention may reduce colour loss by more than 50%, preferably by more than 60%, more preferably by more than 70%, for example by more than 80% or more than 90%.

By a reduction of at least 10% we mean that if a material is treated according to the method of the present invention the colour loss is at least 10% less than if a material is treated with an equivalent method in which the hydroxy substituted aldehyde is not included. For example in the case of a shampoo composition, washing the hair with a shampoo comprising a hydroxy substituted aldehyde provides a 10% reduction in colour loss compared with washing with a shampoo which is otherwise identical but does not contain the hydroxy substituted aldehyde.

Suitably the method of the present invention provides a reduction in colour loss of at least 10%, preferably at least 20%, suitably at least 30%, compared with a control when measured according to the method of example 2. In this regard it should be noted that the control provides a colour loss of 100%. Thus if a colour loss of 90% is observed, this represents a reduction in colour loss of 10%.

The present invention may involve contacting the material with a composition comprising a hydroxy-substituted aldehyde once or more than once.

The invention may be used on a regular basis, for example every time hair (or another material) is washed. Alternatively the invention may be used periodically on a less frequent basis, for example, every week or every month.

It has been surprisingly found that the method of the present invention can significantly reduce the loss of colour from dyed hair.

The present invention may provide reduced colour loss following a number of washes. For example in embodiments in which the invention relates to a colouring composition the inclusion of a hydroxy substituted aldehyde at some stage in the dyeing process may provide improved wash fastness and/or reduced colour fade over time.

Preferably dyeing the hair according to the method of the second aspect provides improved wash fastness. Suitably hair dyed according to the method of the second aspect has colour loss of at least 10% less after three washes compared with hair dyed by an equivalent method excluding the hydroxy substituted aldehyde, preferably at least 30%, more preferably at least 50%.

According to a fourth aspect of the present invention there is provided the use of a hydroxy-substituted aldehyde to combat colour loss from dyed hair.

One especially preferred compound for use in the present invention is 2-hydroxyoctanal.

According to a fifth aspect of the present invention there is provided the compound of formula

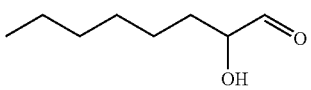

According to a sixth aspect there is provided a method of preparing a compound of the fifth aspect.

The compound of the fifth aspect may be prepared by any suitable method. Such methods will be known to the person skilled in the art. Typically the compounds are formed from corresponding 1,2-diol compounds by selective oxidation of the alpha alcohol. One suitable method is described in example 1.

According to an seventh aspect of the present invention there is provided a composition comprising a compound of the fifth aspect.

Preferably the composition is a hair care composition and preferred features are as defined in relation to the third aspect.

According to an eighth aspect of the present invention there is provided a packaged hair colouring product comprising one or more compositions wherein the one or more compositions together comprise at least one dye compound and/or one dye precursor compound and a hydroxy-substituted aldehyde.

Preferred features of the product of the eighth aspect are as described in relation to the first, second, third and fourth aspects and the product is suitable for use in the colouring method of the second aspect.

In some embodiments the product of the eighth aspect may be a product for oxidative dyeing of the hair comprising a first composition comprising one or more dye precursor compounds and a second oxidising composition comprising one or more oxidising agents. The hydroxy substituted aldehyde may be included in the composition comprising the one or more dye precursor compounds and/or in the composition comprising the oxidising agent. However in preferred embodiments it is provided as a separate third composition. This third composition can be applied to the hair before, during or after treatment with the first and/or second compositions. Alternatively it may be admixed with the first or second composition prior to contact with the hair.

The invention will now be further defined with reference to the following non-limiting examples.

DESCRIPTION OF THE DRAWING

FIG. 1 is a plot showing the reduction in leaching of dye, expressed as the difference in light reflectance at 457 nm, of dyed wool swatches treated with compositions of the invention relative to the control.

EXAMPLE 1

The hydroxy-substituted aldehyde compounds used in the present invention were prepared using the following method:

These are formed from corresponding 1,2-diol compounds by selective oxidation of the alpha alcohol. In a three necked flask, a copper catalyst in a high temperature oil were weighed. The flask was then fitted with side arm, a receiving flask and a water cooled condenser. The reaction was heated with stirring to the correct temperature under a flow of nitrogen and/or vacuum.

The required alcohol was added continuously at a constant rate. The product was collected by distillation from the reaction mixture. The vacuum or nitrogen was adjusted to ensure the aldehyde was distilled over rapidly to reduce the chance of further oxidation. The exact conditions depend on aldehyde being produced. A yield of greater than 75% is typical.

EXAMPLE 2

Wool swatches were dyed with an oxidative red dye formed as follows:

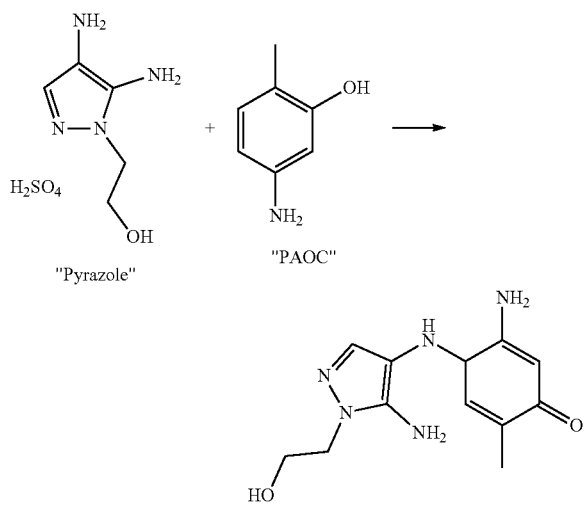

The dyed swatches were immersed in a solution comprising the test compounds listed in table 1 at 2 wt % (except compounds 5, 10, 11 and 12) and 0.1 wt % SLES buffered to pH 5.5 with sodium acetate buffer for 30 minutes at 40° C. The swatches were then rinsed in water for 2 minutes and then dried. A visual assessment was made of the cloth and this was rated on a scale of 1-5, as follows:

1 Colour significantly more intense than control and close to original colour
    2 Colour visibly more intense than control
    3 Colour not visibly more intense than control
    4 Colour visibly less intense than control
    5 Colour significantly less intense than control or colour hue change (eg, blue) or cloth greasy or spotted (reasons recorded)

For cloths visually assessed as more intense than the control (Score 1 or 2), then the actual reading of the colour intensity was measured using standard reflectometry and compared with a deionised water control (containing 0.1 wt % SLES). 100% is the amount of dye removed by the control and a number <100% shows less dye removal than the control and 0% is the colour of the original cloth. In this case the difference in reflectance of light having a wavelength of 457 nm was measured.

Table 1 details the compounds tested and the results obtained. Compounds 1 to 9 are of the invention. Compounds 13 to 20 are comparative examples.

TABLE 1

|    | Compound                   | Score | Result         |
|----|----------------------------|-------|----------------|
| 1  | 2-hydroxypropanal          | 1     | 16%            |
| 2  | 2-hydroxybutanal           | 2     | 64%            |
| 3  | 2-hydroxyhexanal           | 1     | −2%            |
| 4  | 2-hydroxyoctanal           | 1     | 0%             |
| 5  | D-Glyceraldehyde           | 1     | @1 wt % = 15%  |
| 6  | 3-hydroxypropanal          | 2     | 56%            |
| 7  | 3-hydroxybutanal           | 2     | 68%            |
| 8  | 4-hydroxy-cis-butenal      | 2     | 57%            |
| 9  | 6-hydroxy hexanal          | 2     | 56%            |
| 10 | 2-hydroxydecanal           | 2     | @1 wt % = 37%  |
| 11 | 2-hydroxydodecanal         | 2     | @1 wt % = 68%  |
| 12 | 2-hydroxytetradecanal      | 2     | @1 wt % = 56%  |
| 13 | Acetaldehyde               | 3     |                |
| 14 | Propylaldehyde             | 3     |                |
| 15 | Valeraldehyde              | 4     |                |
| 16 | Hexanal                    | 3     |                |
| 17 | Octanal                    | 5     |                |
| 18 | Decanal                    | 3     |                |
| 19 | 3-cyclohexene-1-carboxaldehyde | 3 |                |
| 20 | 2-Deoxy-D-ribose           | 3     |                |

EXAMPLE 3

The wash fastness of the dyeings according to the invention was assessed according to the following method.

Wool swatch samples were initially treated as in example 2. They were then treated with a deionized water composition comprising 0.1% SLES for wetting for 15 minutes, rinsed and dried. The reflectance at 457 nm (R457) was measured. A further two washing steps with deionized water comprising 0.1% SLES were carried out for 30 minutes each.

The results in table 2 are the absolute values of ΔR457 wherein ΔR457 is the difference in reflectance at 457 nm between the initially dyed wool swatches and the swatches that have been treated as detailed in the table.

TABLE 2

| Composition | Aldehyde | 30 min treatment with Aldehyde | Wash 15 min | Wash 45 min (total) | Wash 75 min (total) | % colour loss compared to control |
|---|---|---|---|---|---|---|
| 1 | Glyceraldehyde    | 0.2  | 1.9 | 4.9  | 7.0  | 33   |
| 2 | 2-hydroxy propanal | 1.2  | 3.1 | 6.3  | 8.5  | 40   |
| 3 | 2-hydroxy octanal  | −1.5 | 2.5 | 7.3  | 10.3 | 48.5 |
| 4 | 0.1% SLES (control)| 4.9  | 6.9 | 13.3 | 21.2 | 100  |

The results in table 2 and FIG. 1 clearly show that the present invention provides a benefit in terms of reducing subsequent leaching of dye relative to the control.

EXAMPLE 4

A study of the use of shampoo compositions comprising 2-hydroxy octanal to achieve wash fastness was carried out according to the following method.

Wool swatch samples were treated as in example 2 using 2.5 wt % solutions of 2-hydroxy octanal or deionised water control and 10% of a basic shampoo formula (12.5 wt % SLES, 2.5 wt % CAPB in water). The results in Table 3 are the absolute values of ΔR457 wherein ΔR457 is the difference in reflectance at 457 nm between the initially dyed wool swatches and the swatches that have been treated with the inventive composition or the control.

TABLE 3

| Composition | ΔR457 |
|---|---|
| Shampoo + 2.5 wt % 2-hydroxy octanal | 0.4 |
| Shampoo control | 7.4 |

The invention claimed is:

1. A method of combatting colour loss from a dyed material, the method comprising contacting the material with a composition comprising a hydroxy-substituted aldehyde selected from the group consisting of 2-hydroxydecanal, 2-hydroxydodecanal, 2-hydroxytetradecanal, 2-hydroxyhexanal, 2-hydroxypropanal, 2-hydroxyoctanal, 3-hydroxypropanal, 4-hydroxy-but-2-enal, 2-hydroxybutanal, 3-hydroxybutanal and 4-hydroxybutanal.

2. The method according to claim 1 wherein the material is a keratinous material.

3. The method according to claim 2 wherein the material is human hair or animal hair.

4. The method according to claim 3 wherein the material is growing human hair or animal hair.

5. The method according to claim 1 wherein the composition comprising the hydroxy substituted aldehyde is selected from the group consisting of: a shampoo composition, a conditioning composition, a hair styling composition, a hair permanent waving composition, a hair relaxing composition, a hair permanent straightening composition and a hair coloring composition.

6. The method according to claim 1 wherein the composition comprising the hydroxy substituted aldehyde further comprises 1 to 30 wt % of one or more surfactants.

7. The method according to claim 1 wherein the aldehyde is an alpha-hydroxy aldehyde.

8. The method according to claim 1 wherein the aldehyde is selected from the group consisting of 2-hydroxypropanal, 2-hydroxyhexanal, 2-hydroxyoctanal, 2-hydroxydecanal, and 2-hydroxybutanal.

9. The method according to claim 8 wherein the aldehyde is selected from the group consisting of 2-hydroxypropanal, 2-hydrohexanal, and 2-hydroxyoctanal.

10. The method according to claim 1 comprising a first hydroxy-substituted aldehyde having less than 10 carbon atoms and a second hydroxy-substituted aldehyde having 10 or more carbon atoms.

11. The method according to claim 10 wherein the second hydroxy-substituted aldehyde is selected from the group consisting of 2-hydroxydecanal, 2-hydroxydodecanal and 2-hydroxytetradecanal.

12. The method according to claim 10 wherein the first hydroxy-substituted aldehyde is selected from the group consisting of: 2-hydroxypropanal, 2-hydroxyhexanal and 2-hydroxyoctanal and the second hydroxy-substituted aldehyde is selected from the group consisting of; 2-hydroxydecanal, 2-hydroxydodecanal and 2-hydroxytetradecanal.

13. The method according to claim 1 wherein the composition comprising the aldehyde further comprises an amine of a salt carboxylic acid.

14. The method according to claim 1 wherein the composition comprising the aldehyde further comprises a polycarboxylic acid derived chelating agent.

15. The method according to claim 1 wherein the composition comprising the aldehyde further comprises a succinimidyl ester.

16. The method according to claim 1 wherein the composition comprising the aldehyde further comprises a cross-linking agent comprising two or more maleic acid derived reactive moieties and a linker having two or more amino groups.

17. The method according to claim 1 which reduces colour loss by at least 20% compared with a material dyed by an equivalent method excluding the hydroxy substituted aldehyde.

18. The method according to claim 1 wherein the dyed material is a textile material.

19. The method according to claim 18 which combats colour loss resulting from washing a dyed textile material in a laundry washing process.

* * * * *